US011590267B2

(12) United States Patent
Baldwin et al.

(10) Patent No.: US 11,590,267 B2
(45) Date of Patent: Feb. 28, 2023

(54) MEDICAL DEVICES

(71) Applicant: MicroVention, Inc., Aliso Viejo, CA (US)

(72) Inventors: Aaron Baldwin, Orange, CA (US); Xinping Wu, Aliso Viejo, CA (US); Bryan Fiamengo, Yorba Linda, CA (US); Garrett Ulrich, Huntington Beach, CA (US); John Belletto, Yorba Linda, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 362 days.

(21) Appl. No.: 16/589,816

(22) Filed: Oct. 1, 2019

(65) Prior Publication Data

US 2020/0101204 A1 Apr. 2, 2020

Related U.S. Application Data

(60) Provisional application No. 62/739,633, filed on Oct. 1, 2018.

(51) Int. Cl.

| | |
|---|---|
| ***A61L 33/06*** | (2006.01) |
| ***A61L 31/10*** | (2006.01) |
| ***B05D 3/14*** | (2006.01) |
| ***B05D 7/16*** | (2006.01) |
| ***A61L 31/02*** | (2006.01) |

(52) U.S. Cl.

CPC ........... *A61L 33/062* (2013.01); *A61L 31/022* (2013.01); *A61L 31/10* (2013.01); *B05D 3/142* (2013.01); *B05D 7/16* (2013.01); *A61L 2420/02* (2013.01)

(58) Field of Classification Search

CPC ............................... A61L 33/062; A61L 31/10

See application file for complete search history.

(56) References Cited

U.S. PATENT DOCUMENTS

| | | | | |
|---|---|---|---|---|
| 5,607,475 A * | 3/1997 | Cahalan | A61L 27/34 623/924 |
| 6,599,558 B1 * | 7/2003 | Al-Lamee | A61L 31/10 427/407.1 |
| 6,613,432 B2 | 9/2003 | Zamora et al. | |
| 7,910,678 B2 * | 3/2011 | Pacetti | A61L 27/54 526/320 |
| 8,858,618 B2 * | 10/2014 | Anzai | A61L 31/10 623/1.42 |
| 2004/0117006 A1 | 6/2004 | Lewis et al. | |
| 2005/0220842 A1 | 10/2005 | Dewitt et al. | |
| 2006/0246209 A1 * | 11/2006 | McNiven | A61L 31/10 427/2.1 |
| 2008/0125560 A1 | 5/2008 | Pacetti | |
| 2008/0286332 A1 | 11/2008 | Pacetti | |
| 2008/0286333 A1 * | 11/2008 | Kangas | A61L 31/16 525/50 |
| 2009/0192583 A1 * | 7/2009 | Tedeschi | A61L 31/10 623/1.42 |
| 2011/0046337 A1 * | 2/2011 | Basil | C09D 183/04 528/41 |
| 2011/0104508 A1 | 5/2011 | Wang et al. | |
| 2013/0231433 A1 * | 9/2013 | Date | C08L 23/10 524/505 |
| 2013/0243396 A1 | 9/2013 | Kummer | |
| 2016/0083610 A1 | 3/2016 | Lin et al. | |
| 2017/0232156 A1 | 8/2017 | Ma et al. | |

FOREIGN PATENT DOCUMENTS

| | | |
|---|---|---|
| CN | 103751841 A | 4/2014 |
| CN | 103193927 B | 1/2016 |
| WO | 2013/130850 A1 | 9/2013 |
| WO | 2020/072481 A1 | 4/2020 |

OTHER PUBLICATIONS

International Search Report and Written Opinion, dated Jan. 6, 2020, for International Application No. PCT/US2019/054047 filed on Oct. 1, 2019.

Crowley et al., A Healthy Future: Platinum in Medical Applications. Platinum Metals Rev., 55(2):98-107 (2011).

* cited by examiner

*Primary Examiner* — Cachet I Proctor

(74) *Attorney, Agent, or Firm* — K&L Gates LLP; Louis C. Cullman; Benjamin D. Heuberger

(57) ABSTRACT

Described are medical devices including expandable tubular bodies configured to be implanted into a lumen, wherein the outer surface of the expandable tubular bodies are coupled to a polymer(s).

20 Claims, No Drawings

MEDICAL DEVICES

RELATED APPLICATION

This application claims the priority of U.S. Provisional Patent Application No. 62/739,633, filed Oct. 1, 2018, the entire content of which is incorporated herein by reference.

FIELD

Described herein are medical devices, including stents and flow diverters, with covalently bonded polymer coatings that can reduce thrombogenicity. Methods of making and using the medical devices are also described.

SUMMARY

Described herein are medical device coatings. The device coatings can be used for any medical devices that may come into contact with tissue and/or blood. In some embodiments, the coatings can prevent or reduce thrombus formation around a device when compared to an uncoated device.

Expandable, tubular bodies, including stents and flow diverters, are widely used in the medical field to treat a variety of vascular conditions, including stenosis and dilatation or weakening of arterial walls (i.e., aneurysm). For the treatment of stenosis, a stent is inserted into the blockage of the vessel and deployed. The stent buttresses the blockage out of the lumen of the vessel, restoring blood flow. For the treatment of an intracranial aneurysm, a stent may be deployed across the neck of the aneurysm to provide support for subsequent coiling of the aneurysm. Alternatively, a flow diverter may be deployed across the neck of the aneurysm to reduce or eliminate the exposure of the aneurysm wall to blood flow.

While stents and flow diverters are widely used to successfully treat various vascular conditions, they are not without limitations. One such limitation is the requirement of anti-platelet therapy to prevent thrombosis of the stent. Currently, dual antiplatelet therapy is the standard of care. Low dose aspirin is recommended indefinitely. A P2Y12 inhibitor (i.e., clopidogrel, prasugrel, ticagrelor, or cangrelor) is recommended for up to 12 months post-procedure. While dual antiplatelet therapy is effective for maintaining the lumen of the stented vessel, bleeding (i.e., gastrointestinal or intracranial) complications can arise as well as other complications (e.g., stent induced thrombosis). While not frequent, these complications are associated with morbidity and mortality. As a result, efforts to reduce or eliminate dual antiplatelet therapy are being performed.

One such coating to reduce the thrombogenicity of stents is phosphorylcholine. In such an embodiment, a cobalt-chrome braided flow diverter is covalently coupled with phosphorylcholine in effort to reduce thrombogenicity. A reduction in thrombogenicity of the coated flow diverters compared to the uncoated flow diverters using the thrombogram test can be seen.

Another coating to potentially reduce the thrombogenicity of stents is heparin. In such an embodiment, a heparin coating is dip-coated or spray-coated over a stent in effort to reduce thrombogenicity. However, effects of the heparin coating in reducing thrombogenicity are not known.

Anti-thrombotic coatings can be performed on tubular, expandable devices as well as on a wide range of blood contacting medical devices, including tubing, catheters, cardiopulmonary bypass, and blood oxygenators. For example, a polymeric coating comprising poly(methoxyethyl acrylate) has been developed for the coating of blood gas oxygenators. This polymer is coated on every surface of the perfusion circuit to reduce thrombogenicity. However, this polymer is simply adsorbed to the surface and is suitable only for equipment that will be used for a short period of time.

Many other molecules have been evaluated for the coating of stents, flow diverters, and other blood contacting medical devices. However, a satisfactory, durable coating has not been found.

Described herein are tubular, expandable devices. These devices can be configured to be implanted in the vasculature or other body lumen. The medical device surface is coupled to an activated copolymer that can reduce the thrombogenicity of the tubular, expandable device. In some embodiments, the coupling is through a covalent linkage.

In one embodiment, the tubular, expandable devices include of a plurality of braided filaments woven into a configuration to be implanted into a vessel. The braided filaments can be metallic. The metallic composition can include gold, silver, copper, steel, aluminum, titanium, cobalt, chromium, platinum, nickel, combinations thereof, alloys thereof such as, but not limited to nitinol (nickel-titanium), cobalt-nickel, cobalt-chromium, platinum-tungsten, and combinations thereof. The braided filaments can by polymeric. The polymeric braided filaments can comprise hydroxyl groups, e.g., on a surface of the filaments.

In another embodiment, the tubular, expandable devices can include a polymeric tube laser cut into a configuration to be implanted into a vessel. The polymeric tube may include hydroxyl groups, e.g., on a surface of the polymeric tube.

In another embodiment, the tubular, expandable devices can include a metallic tube laser cut into a configuration to be implanted into a vessel. The metallic tube may include gold, silver, copper, steel, aluminum, titanium, cobalt, chromium, platinum, nickel, combinations thereof, alloys thereof such as, but not limited to nitinol (nickel-titanium), cobalt-nickel, cobalt-chromium, platinum-tungsten, and combinations thereof.

In one embodiment, the activated copolymer can be prepared by copolymerizing a first monomer, e.g., an alkoxyalkylacrylate or a derivative thereof, with a second monomer, e.g., a silane containing monomer.

In one embodiment, the first monomer is of Formula (I):

(I)

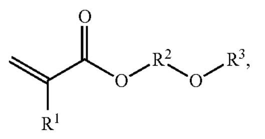

wherein $R^1$ is H or —$C_{1-4}$ alkyl, $R^2$ is —$C_{1-4}$ alkylene, and $R^3$ is —$C_{1-4}$ alkyl;

or the first monomer is of Formula (II):

(II)

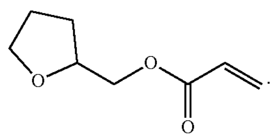

In some embodiments, the first monomer is of Formula (I). In some embodiments, the first monomer is of Formula (II).

In some embodiments, $R^1$ is H, methyl, ethyl, propyl, or butyl. In some embodiments, $R^1$ is H or methyl.

In some embodiments, $R^2$ is methylene, ethylene, propylene, or butylene. In some embodiments, $R^2$ is methylene or ethylene.

In some embodiments, $R^3$ is methyl, ethyl, propyl, or butyl. In some embodiments, $R^3$ is methyl.

In some embodiments, $R^1$ is methyl and $R^3$ is methyl.

In one embodiment, the first monomer is methoxyethyl acrylate (e.g., 2-methoxyethyl acrylate) or methoxyethyl methacrylate (e.g., 2-methoxyethyl methacrylate).

In one embodiment the second monomer comprises 1) a polymerizable site such as an acrylate, methacrylate, acrylamide, or a combination thereof, and 2) a silane such as a monoalkoxy silane, a dialkoxy silane, a trialkoxy silane, or a combination thereof.

In one embodiment, the second monomer is of Formula (III):

(III)

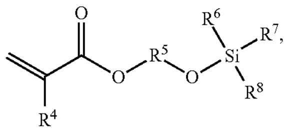

wherein $R^4$ is H or —$C_{1-4}$ alkyl, $R^5$ is —$C_{1-4}$ alkylene, $R^6$ is —O—($C_{1-4}$ alkyl), $R^7$ is —$C_{1-4}$ alkyl or —O—($C_{1-4}$ alkyl), and $R^8$ is —$C_{1-4}$ alkyl or —O—($C_{1-4}$ alkyl).

In some embodiments, $R^4$ is H or —$CH_3$. In some embodiments, $R^3$ is —$CH_3$. In some embodiments, $R^4$ is —$CH_3$ and $R^6$ is —$OCH_3$.

In some embodiments, $R^5$ is methylene, ethylene, propylene, or butylene.

In some embodiments, $R^6$ is —O-methyl, —O-ethyl, —O-propyl, or —O-butyl.

In some embodiments, $R^7$ is methyl, ethyl, propyl, butyl, —O-methyl, —O-ethyl, —O-propyl, or —O-butyl.

In some embodiments, $R^8$ is methyl, ethyl, propyl, butyl, —O-methyl, —O-ethyl, —O-propyl, or —O-butyl.

In some embodiments, $R^6$ is —O-methyl, —O-ethyl, —O-propyl, or —O-butyl, $R^7$ is methyl, ethyl, propyl, or butyl, and $R^8$ is methyl, ethyl, propyl, or butyl.

In some embodiments, $R^6$ is —O-methyl, —O-ethyl, —O-propyl, or —O-butyl, $R^7$ is —O-methyl, —O-ethyl, —O-propyl, or —O-butyl, and $R^8$ is methyl, ethyl, propyl, or butyl.

In some embodiments, $R^6$ is —O-methyl, —O-ethyl, —O-propyl, or —O-butyl, $R^7$ is —O-methyl, —O-ethyl, —O-propyl, or —O-butyl, and $R^8$ is —O-methyl, —O-ethyl, —O-propyl, or —O-butyl.

In one embodiment, the second monomer is (3-acryloxypropyl)dimethylmethoxysilane, (3-acryloxypropyl)methyldiethoxysilane, (3-acryloxypropyl)methyldimethoxysilane, (3-acryloxypropyl)trimethoxysilane, (3-methacrylamidopropyl)trimethoxysilane, (methacryloxymethyl)dimethylethoxysilane, (methacryloxymethyl)methyldimethoxysilane, (methacryloxymethyl)methyldiethoxysilane, 3-acrylamidopropyltrimethoxysilane, acryloxymethyltrimethoxysilane, methacryloxymethyltriethoxysilane, methacryloxymethyltrimethoxysilane, methacryloxypropyldimethylethoxysilane, methacryloxypropyldimethylmethoxysilane, methacryloxypropylmethyldiethoxysilane, methacryloxypropylmethyldimethoxysilane, methacryloxypropyltriethoxysilane, methacryloxypropyltrimethoxysilane, or a combination thereof.

In some embodiments the activated copolymer can be prepared by copolymerizing one or more first monomers provided herein with one or more second monomers provided herein.

In one embodiment, the first monomer is of Formula (I) and the second monomer is of Formula (III). In one embodiment, the first monomer is of Formula (II) and the second monomer is of Formula (III).

In one embodiment, the first monomer is methoxyethyl acrylate (e.g., 2-methoxyethyl acrylate) or methoxyethyl methacrylate (e.g., 2-methoxyethyl methacrylate), or a combination thereof, and the second monomer is (3-acryloxypropyl)dimethylmethoxysilane, (3-acryloxypropyl)methyldiethoxysilane, (3-acryloxypropyl)methyldimethoxysilane, (3-acryloxypropyl)trimethoxysilane, (3-methacrylamidopropyl)trimethoxysilane, (methacryloxymethyl)dimethylethoxysilane, (methacryloxymethyl)methyldimethoxysilane, (methacryloxymethyl)methyldiethoxysilane, 3-acrylamidopropyltrimethoxysilane, acryloxymethyltrimethoxysilane, methacryloxymethyltriethoxysilane, methacryloxymethyltrimethoxysilane, methacryloxypropyldimethylethoxysilane, methacryloxypropyldimethylmethoxysilane, methacryloxypropylmethyldiethoxysilane, methacryloxypropylmethyldimethoxysilane, methacryloxypropyltriethoxysilane, methacryloxypropyltrimethoxysilane, or a combination thereof.

In some embodiments, the ratio of the first monomer to the second monomer is about 50:50 to about 99:1. In some embodiments, the ratio of the second monomer to the first monomer is about 50:50 to about 99:1.

Methods of coating an implantable medical device are also described. The methods can include activating a surface of the implantable medical device by hydroxylation, and coupling an activated copolymer formed from a first monomer, e.g., an alkoxyalkylacrylate or a derivative thereof, with a second monomer, e.g., a silane containing monomer to the activated surface.

In some embodiments, the methods comprise hydroxylation of the surface using oxygen plasma, water plasma, or hydrogen peroxide to generate an activated surface. In some embodiments, the methods comprise hydroxylation of the surface using oxygen plasma to generate an activated surface.

In some embodiments, the method further includes argon plasma treatment after hydroxylation.

DETAILED DESCRIPTION

The medical devices described herein may be any material or device that contacts blood flow, including oxygenators, artificial blood vessels, cardiopulmonary bypass machines, catheters, guidewires, stents, flow diverters, venous filters, distal protection devices, tubing, stent-grafts, and the like. In some embodiments, the medical device is a stent or flow diverter. In other embodiments, the medical device is a braided stent or flow diverter.

At least a portion of a medical device surface can be coated. In some embodiments, portions of a medical device may be masked using the herein described coatings. In some embodiments, at least about 10%, at least about 20%, at least about 30%, at least about 40%, at least about 50%, at least about 60%, at least about 70%, at least about 80%, at least about 90%, at least about 95%, or at least about 95% of the medical device surface can be coated.

The surfaces of the medical devices can be treated/coated to reduce thrombogenicity. The medical devices can include a surface treatment to reduce thrombogenicity as well as methods for application of the coatings to medical devices.

The substrate for the coating may be any suitable material, including metals, glass, polymers, ceramics, combinations thereof, and the like. In some embodiments, the substrate is a metal. While any metallic surface may be used, suitable metals can include gold, silver, copper, steel, aluminum, titanium, cobalt, chromium, platinum, nickel, alloys thereof, and combinations thereof. Suitable alloys can include nitinol (nickel-titanium), cobalt-nickel, cobalt-chromium, and platinum-tungsten. In one embodiment, the substrate is a combination of nitinol and platinum-tungsten. In some embodiments, the substrate is a polymer. In some embodiments, the suitable material can be activated by hydroxylation.

A polymer of the reduced thrombogenicity coating can be prepared by polymerization of two or more monomers, e.g., a first monomer and a second monomer as provided herein.

In one embodiment, to prepare the polymer, the two or more monomers and an initiator are dissolved in a solvent. In general, any solvent that dissolves the two or more monomers and the initiator can be used. Suitable solvents can include methanol/water, ethanol/water, isopropanol/water, dioxane/water, tetrahydrofuran/water, dimethylformamide/water, dimethylsulfoxide and/or water, and combinations thereof. With carboxylic acid and hydroxyl containing monomers, a wider range of solvents can be utilized, including toluene, xylene, dimethylsulfoxide, dioxane, THF, methanol, ethanol, and dimethyl formamide.

Polymerization initiators can be used to start the polymerization of the monomers in the solution. The polymerization can be initiated by reduction-oxidation, radiation, heat, or any other method known in the art. Radiation cross-linking of the monomer solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the monomer solution.

In some embodiments, an initiator may not be used.

In one embodiment, the polymerization initiator is azobisisobutyronitrile (AlBN) or a water soluble AlBN derivatives (2,2'-azobis(2-methylpropionamidine) dihydrochloride), or 4,4'-azobis(4-cyanopentanoic acid). Other suitable initiators include N,N,N',N'-tetramethylethylenediamine, ammonium persulfate, benzoyl peroxides, and combinations thereof, including azobisisobutyronitriles. Initiator concentrations can range from about 0.25% to about 2% w/w of the mass of the monomers in solution. The polymerization reaction can be performed at elevated temperatures, such as in the range from about 65 to about 85° C. After the polymerization is completed, the polymer can be recovered by precipitation in a non-solvent and dried under vacuum.

In some embodiments, the polymers described herein can have a molecular weight of greater than about 10,000 g/mol, between about 10,000 g/mol and about 200,000 g/mol, between about 8,000 g/mol and about 200,000 g/mol, between about 100,000 g/mol and about 200,000 g/mol, between about 50,000 g/mol and about 200,000 g/mol, between about 25,000 g/mol and about 200,000 g/mol, between about 8,000 g/mol and about 100,000 g/mol, between about 10,000 g/mol and about 100,000 g/mol, between about 50,000 g/mol and about 100,000 g/mol, between about 75,000 g/mol and about 100,000 g/mol, between about 75,000 g/mol and about 200,000 g/mol, about 10,000 g/mol, about 50,000 g/mol, about 100,000 g/mol, about 150,000 g/mol, or about 200,000 g/mol.

In one embodiment, the polymer is applied to the substrate in several steps, each of which may or may not be optional. In some embodiments, the polymer is applied to the substrate in three steps. The necessity of each step is driven by the selection of the substrate.

Step 1 includes cleaning. To clean the substrate, it can be incubated in acetone, methanol, ethanol, isopropyl alcohol, water, or a combination thereof under sonication. The duration of each washing step ranges from about 1 minute to about 20 minutes. The temperature of sonication can range from about 18 to about 55° C. Following the conclusion of Step 1, the substrate moves to Step 2. In some embodiments, Step 2 immediately follows Step 1.

In some embodiments, cleaning can optionally include cleaning with soap/detergent and water.

Step 2 includes hydroxylation, a treatment to increase the number of hydroxyl groups on the surface of the substrate. The surface to be treated may be hydroxylated using a number of different oxidizers, including acids, bases, peroxides, plasma treatment, and combinations thereof.

Acids for treatment include hydrochloric acid, nitric acid, sulfuric acid, hydrofluoric acid, perchloric acid, and combinations thereof. Bases for treatment include sodium hydroxide, ammonium hydroxide, and combinations thereof. Peroxides for treatment include hydrogen peroxide, t-butyl peroxide, and combinations thereof. In one embodiment, an oxidizer is hydrogen peroxide. The oxidizer used for hydroxylation may be in concentration from about 1% to about 100%. The hydroxylation duration can range from about 0.25 hr to about 4 hr at temperatures ranging from about 18 to about 100° C. After hydroxylation, the substrate may be washed in acetone, methanol, ethanol, isopropyl alcohol, water, or combination thereof, with or without sonication. Each wash can range from about 1 minute to about 15 minutes in duration. Drying under vacuum may optionally follow washing. In one embodiment, a hydroxylation utilizes about 10% hydrogen peroxide at about 100° C. for about 45 minutes followed by about 5 min sequential washes in water, ethanol, and acetone followed by drying under vacuum.

In another embodiment oxygen plasma is used for treatment. The substrate can be exposed to oxygen plasma in a plasma treatment machine. Plasma treatment parameters can include oxygen flow, watts, pressure, and time. Oxygen flow can be from about 1-500 sccm, about 1-250 sccm, about 1-120 sccm, about 100-500 sccm, about 100-200 sccm, about 100-140 sccm, at least about 100 sccm, at least about 50 sccm, or less than about 500 sccm. Power can be from about 1-600 watts, about 1-500 watts, about 1-400 watts, about 100-600 watts, about 200-600 watts, about 400-600 watts, at least about 400 watts, at least about 500 watts, or less than about 600 watts. Pressure can be from about 120-2000 mTorr, about 200-2000 mTorr, about 200-1000 mTorr, about 300-500 mTorr, about 300-2000 mTorr, at least about 200 mTorr, at least about 300 mTorr, or less than about 2000 mTorr. Time can be from about 1-15 minutes, about 5-15 minutes, about 5-10 minutes, at least about 5 minutes, at least about 4 minutes, at least about 3 minutes, at least about 2 minutes, or at least about 1 minute. In one embodiment the oxygen flow is about 120 sccm, the power is about 500 watts, the pressure is about 400 mTorr, and the time is about 5 minutes.

Following hydroxylation, the substrate may be optionally plasma treated with an argon plasma to clean the surface.

Plasma treatment parameters can include argon flow, watts, pressure, and time. Argon flow can be from about 1-500 sccm, about 1-250 sccm, about 1-120 sccm, about 100-500 sccm, about 100-200 sccm, about 100-140 sccm, at least about 100 sccm, at least about 50 sccm, or less than about 500 sccm. Power can be from about 1-500 watts, about 1-400 watts, about 1-300 watts, about 100-500 watts, about 200-500 watts, about 200-400 watts, at least about 100 watts, at least about 200 watts, or less than about 500 watts. Pressure can be from about 120-2000 mTorr, about 200-2000 mTorr, about 200-1000 mTorr, about 300-500 mTorr, about 300-2000 mTorr, at least about 200 mTorr, at least about 300 mTorr, or less than about 2000 mTorr. Time can be from about 1-15 minutes, about 5-15 minutes, about 5-10 minutes, at least about 5 minutes, at least about 4 minutes, at least about 3 minutes, at least about 2 minutes, or at least about 1 minute. In one embodiment the argon flow is about 365 sccm argon flow, the power is about 300 watts, and the pressure is about 500 mTorr for about 10 minutes.

Step 3 includes activated copolymer coupling, a treatment to covalently couple the activated copolymer to the substrate. Following plasma treatment, the substrate can be placed in an activated copolymer (copolymer comprising a silane): solvent system in order to couple the activated copolymer to the substrate. During this step, the functional group imparted to the polymer from the second or more monomer can be reacted to the hydroxyl group imparted to the substrate via hydroxylation. In this step, the polymer can be dissolved in water, buffer, methanol, ethanol, isopropanol, butanol, dimethyl formamide, dimethyl sulfoxide, ethyl acetate, toluene, chloroform, dichloromethane, or a combination thereof. The solvent for this step can be 50% v/v ethanol:50% v/v citric buffer in water pH 7. The concentration of the polymer in the solvent can range from about 0.5% to about 95% in the solvent. In one embodiment, the concentration of the polymer in the solvent is about 1%. The duration of the incubation ranges from about 1-48 hrs (e.g., about 6 hrs to about 24 hrs) at a temperature range from about 18 to about 55° C. The coupling may optionally be performed with shaking at a rate from about 100 rpm to about 250 rpm. In one embodiment, coupling conditions are incubation for about 18 hours at room temperature with shaking at about 150 rpm.

After coupling, the substrate may be rinsed in ethanol, methanol, isopropanol, toluene, water, butanol, dimethyl formamide, dimethyl sulfoxide, ethyl acetate, chloroform, dichloromethane, and combinations thereof. In one embodiment, a rinse is ethanol. The copolymer layer may then be cured at temperature ranging from about 30 to about 150° C. for a duration ranging from about 5 min to 60 min. Curing conditions can be about 110° C. for about 30 min.

The polymer solution may be applied to the substrate by dip coating, spraying, brushing, or a combination thereof. In one embodiment, the substrate may be immersed in a an activated copolymer solution for about 1 hour to about 48 hours. In one embodiment, the immersion duration is about 18 hours. The incubation may be conducted at temperatures ranging from about 18 to about 100° C. In one embodiment, the temperature is room temperature. The coupling reaction may optionally be performed with shaking at a rate from about 100 rpm to about 250 rpm. In one embodiment, shaking conditions are about 150 rpm.

After the incubation, the substrate may optionally be rinsed ethanol, methanol, isopropanol, toluene, water, butanol, dimethyl formamide, dimethyl sulfoxide, ethyl acetate, chloroform, dichloromethane, and combinations thereof. In one embodiment, rinsing is in 50% v/v ethanol:50% v/v water. After rinsing, the substrate may be dried using heat or vacuum. The substrate may be heated at temperatures ranging from about 40° C. to about 100° C., with or without vacuum. In some embodiments, drying conditions are 40° C. under vacuum. After drying, the substrate can be sterilized and packaged.

The coated devices can be sterilized without substantially degrading the coating. After sterilization, at least about 50%, about 60%, about 70%, about 80%, about 90%, about 95% about 99% or about 100% of the coating can remain intact. In one embodiment, the sterilization method can be autoclaving, gamma irradiation, pressure sterilization, and/or steam sterilization.

The coatings described herein can prevent the growth of thrombin. In some embodiments, the coatings can reduce the amount of wet thrombin formation by about 50% to about 90%, about 70% to about 90%, about 70% to about 100%, at least about 60%, or at least about 70%. In some embodiments, the coatings can reduce the amount of thrombin formation, when measured dry, by about 60% to about 95%, about 70% to about 95%, about 70% to about 100%, at least about 70%, at least about 80%. or at least about 90%.

Example 1

Preparation of the Braided Medical Device for Hydroxylation

First, the braided medical device is pre-cleaned using sequential incubations in acetone, ethanol, and water for 5 minutes each while sonicating. The cleaned braided medical device is incubated in a solution of 10% hydrogen peroxide in water for 45 minutes at 100° C. and then rinsed three times with water. The braided medical device is cleaned using sequential incubations in water, ethanol, and acetone for 5 minutes each while sonicating. Finally, the braided medical device is dried under vacuum for 18 hours.

Example 2

Hydroxylation of the Braided Medical Device Via Oxygen Plasma

First, the braided medical device is pre-cleaned using sequential incubations in acetone, ethanol, and water for 5 minutes each while sonicating. Then, the braided medical devices are transferred to a vacuum oven and dried under reduced pressure at 40° C. for 30 min. The dried braided medical devices are activated on an IoN 40 Plasma Processing System instrument, using the following parameters:

| | | |
|---|---|---|
| Flow (Oxygen) | 120 +− 10 | sccm |
| Watts | 500 | watts |
| Pressure | 400 | mTorr |
| Time | 5 | minutes |

The activated braided medical devices are then stored in vials.

Example 3

Preparation of a Copolymer of a Monomer of Formula (I) and a Monomer of Formula (III)

To a mixture of 40 mL water and 40 mL methanol, 40 g of a monomer of Formula (I), 4 g of a monomer of Formula (III), and 440 mg of azobisisobutyronitrile are dissolved. Polymerization occurs over 20 hours at 65° C. The copolymer is recovered by precipitation in a mixture of isopropanol:hexanes (500 mL:500 mL). The copolymer is re-dissolved in 100 mL tetrahydrofuran and re-precipitated in a mixture of isopropanol:hexanes (400 mL:600 mL). The copolymer is re-dissolved in 100 mL tetrahydrofuran and re-precipitated in a mixture of isopropanol:hexanes (300 mL:700 mL). The copolymer is redissolved in 100 mL tetrahydrofuran and reprecipitated in a mixture of isopropanol:hexanes (200 mL:800 mL). Finally, the copolymer is stirred in 1 L of hexane for 1 hour and dried under vacuum.

Example 4

Preparation of the Coated, Braided Medical Device Using a Copolymer of a Monomer of Formula (I) and a Monomer of Formula (III)

The copolymer of Example 3 is dissolved in 50%/50% of ethanol/citric buffer 7.0 pH (v/v) at a final concentration of 10 mg/mL. The braided medical device of Example 2 is placed into a vial containing the copolymer solution and incubated for 18 hours at room temperature on the orbital shaker at 150 rpm. After incubation, the device is rinsed with 50%/50% ethanol/water and cured at 40° C. for 30 minutes under vacuum.

Example 5

Evaluation of the Coated, Braided Medical Device Using the Chandler Loop Model

PVC tubing (4 mm inner diameter and 6 mm outer diameter, 54.86 cm length) is measured and cut to fit on the cradle of the Chandler loop instrument (Industriedesign, Neuffen, Germany). A single pre-weighed coated, braided medical device (4.5 mm×2 cm) is deployed into the tubing. Bovine blood is freshly collected from a local slaughterhouse and heparinized at 1 U/mL. The activation clotting time (ACT) is adjusted to be between 150 and 250 seconds with protamine, if necessary. The tubing is filled with blood and the tubing is sealed with a connector. The loop is fit onto a polycarbonate stabilization disk, which is then fixed onto the Chandler Loop instrument. The loops are rotated for 2 hours at a shear rate of 300 $s^{-1}$ at 37° C.

The assemblies are then taken out of the Chandler loop instrument and the blood is drained into PTFE beakers. The ACT of the drained blood is determined. The tubing is thoroughly rinsed with PBS three times to remove any residual blood. The tubing is longitudinally cut with a razor blade and the braided medical device is retrieved and photographed. The stent is weighed (wet weight) and then dried at 37° C. until the weight is constant (dry weight).

Example 6

Evaluation of the Coated, Braided Medical Device Using X-ray Photoelectron Spectroscopy The struts of the braided medical device are analyzed using x-ray photoelectron spectroscopy to determine elemental composition.

Example 7

Evaluation of the Coated Medical Device Using Thrombogram

Thrombogram is performed on a Thrombinoscope instrument (Thrombinoscope B. V., Maastricht, Netherlands) in accordance with the manual. On a 96-well plate, the negative controls, test articles, and thrombin calibrator are arrayed with 9 replicates per group. Platelet-poor plasma (PPP, 240 μL) is added to all the wells and PPP-reagent (60 μL) is added to the negative control and test articles. After the FluCa solution has been added to the instrument, the start button is pressed and the 96 well plate was inserted into the instrument, starting the 10 minute incubation. At the conclusion of the incubation, the results are processed and reported.

Example 8

Evaluation of the Coated, Braided Medical Device Using Blood Loop

The Example 7 braided medical devices are packaged into a delivery system and sterilized with E-beam. PVC tubing inner-lined with X-coating (OD=5/16", ID=3/16", Terumo, Japan) is cut into 140 cm length. The tubing is filled with saline and three identical devices are deployed into the tubing. Saline is then replaced with ovine blood (heparinized at 1 U/mL), and the ACT of the blood is between 150 to 250 seconds. To begin the test, the tubing is closed with tubing connector into a loop and loaded onto a peristaltic pump. While incubating the loop in a heating chamber, blood is circulated inside the loop at 273s-1 for 2 hours ±30 min. At the end of the incubation, blood is drained from each loop and the ACT is measured. The full length of the tubing is rinsed with saline. The stent is cut out of the tubing, weighed (wet weight), and then dried at 37° C. until the weight is constant (dry weight).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

As used herein, the term "alkoxyl" alone or in combination with other terms means, unless otherwise stated, an alkyl group having the designated number of carbon atoms, as defined herein, connected to the rest of the molecule via an oxygen atom.

As used herein, the term "alkyl" alone or in combination with other terms means, unless otherwise stated, a straight or branched chain hydrocarbon having the number of carbon atoms designated (i.e., $C_{1-4}$ means one to four carbon atoms) and includes straight or branched chain substituent groups.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An article of manufacture, comprising an outer surface coupled to a polymer prepared from the free radical polymerization of:

at least one first monomer selected from alkoxyalkylacrylates or (tetrahydrofuran-2-yl)methyl acrylate; and at least one second monomer selected from silane containing monomers.

2. The article of manufacture of claim 1, wherein:

the alkoxyalkylacrylate is of the formula:

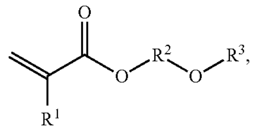

wherein $R^1$ is H or —$C_{1-4}$ alkyl, $R^2$ is —$C_{1-4}$ alkylene, and $R^3$ is —$C_{1-4}$ alkyl.

3. The article of manufacture of claim 2, wherein the polymer is prepared from the free radical polymerization of:

the at least one alkoxyalkylacrylate; and the at least one silane containing monomer.

4. The article of manufacture of claim 2, wherein:

$R^1$ is H or methyl; and $R^2$ is methylene or ethylene.

5. The article of manufacture of claim 2, wherein:

$R^1$ is methyl; and $R^3$ is methyl.

6. The article of manufacture of claim 2, wherein:

the first monomer is a methoxyethyl acrylate, a methoxyethyl methacrylate, or a combination thereof;

and the second monomer is (3-acryloxypropyl)dimethylmethoxysilane, (3-acryloxypropyl)methyldiethoxysilane, (3-acryloxypropyl)methyldimethoxysilane, (3-acryloxypropyl)trimethoxysilane, (3-methacrylamidopropyl)trimethoxysilane, (methacryloxymethyl)dimethylethoxysilane, (methacryloxymethyl)methyldimethoxysilane, (methacryloxymethyl) methyldiethoxysilane, 3-acrylamidopropyltrimethoxysilane, acryloxymethyltrimethoxysilane, methacryloxymethyltriethoxysilane, methacryloxymethyltrimethoxysilane, methacryloxypropyldimethylethoxysilane, methacryloxypropyldimethylmethoxysilane, methacryloxypropylmethyldiethoxysilane, methacryloxypropylmethyldimethoxysilane, methacryloxypropyltriethoxysilane, methacryloxypropyltrimethoxysilane, or a combination thereof.

7. The article of manufacture of claim 6, wherein the first monomer is 2-methoxyethyl acrylate, 2-methoxyethyl methacrylate, or a combination thereof.

8. The article of manufacture of claim 2, wherein the ratio of the first monomer to the second monomer is about 50:50 to about 99:1, or the ratio of the second monomer to the first monomer is about 50:50 to about 99:1.

9. The article of manufacture of claim 2, wherein the second monomer is (3-acryloxypropyl)dimethylmethoxysilane, (3-acryloxypropyl)methyldiethoxysilane, (3-acryloxypropyl)methyldimethoxysilane, (3-acryloxypropyl)trimethoxysilane, (3-methacrylamidopropyl)trimethoxysilane, (methacryloxymethyl)dimethylethoxysilane, (methacryloxymethyl)methyldimethoxysilane, (methacryloxymethyl) methyldiethoxysilane, 3-acrylamidopropyltrimethoxysilane, acryloxymethyltrimethoxysilane, methacryloxymethyltriethoxysilane, methacryloxymethyltrimethoxysilane, methacryloxypropyldimethylethoxysilane, methacryloxypropyldimethylmethoxysilane, methacryloxypropylmethyldiethoxysilane, methacryloxypropylmethyldimethoxysilane, methacryloxypropyltriethoxysilane, methacryloxypropyltrimethoxysilane, or a combination thereof.

10. The article of manufacture of claim 2, wherein the silane containing monomer is of the formula:

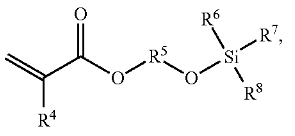

wherein $R^4$ is H or —$C_{1-4}$ alkyl, $R^5$ is —$C_{1-4}$ alkylene, $R^6$ is —O—($C_{1-4}$ alkyl), $R^7$ is —$C_{1-4}$ alkyl or —O—($C_{1-4}$ alkyl), and $R^8$ is —$C_{1-4}$ alkyl or —O—($C_{1-4}$ alkyl).

11. The article of manufacture of claim 10, wherein:

$R^3$ is —$CH_3$; and $R^4$ is H or —$CH_3$.

12. The article of manufacture of claim 10, wherein:

$R^4$ is —$CH_3$; and $R^6$ is —$OCH_3$.

13. The article of manufacture of claim 10, wherein:

$R^6$ is —O-methyl, —O-ethyl, —O-propyl, or —O-butyl;

$R^7$ is methyl, ethyl, propyl, or butyl; and $R^8$ is methyl, ethyl, propyl, or butyl.

14. The article of manufacture of claim 10, wherein:

$R^6$ is —O-methyl, —O-ethyl, —O-propyl, or —O-butyl;

$R^7$ is —O-methyl, —O-ethyl, —O-propyl, or —O-butyl; and $R^8$ is methyl, ethyl, propyl, or butyl.

15. The article of manufacture of claim 10, wherein:

$R^6$ is —O-methyl, —O-ethyl, —O-propyl, or —O-butyl;

$R^7$ is —O-methyl, —O-ethyl, —O-propyl, or —O-butyl; and $R^8$ is —O-methyl, —O-ethyl, —O-propyl, or —O-butyl.

16. The article of manufacture of claim 1, wherein the article of manufacture includes a metal that is a combination of nitinol and platinum-tungsten.

17. The article of manufacture of claim 1, wherein the polymer is covalently coupled to the outer surface.

18. The article of manufacture of claim 1, wherein the polymer is prepared from the free radical polymerization of:

(tetrahydrofuran-2-yl)methyl acrylate; and the at least one silane containing monomer.

19. The article of manufacture of claim 1, wherein the second monomer comprises:

1) an acrylate, a methacrylate, an acrylamide, or a combination thereof; and 2) a monoalkoxy silane moiety, a dialkoxy silane moiety, a trialkoxy silane moiety, or a combination thereof.

20. The article of manufacture of claim 1, wherein the second monomer is (3-acryloxypropyl)dimethyl methoxysilane, (3-acryloxypropyl)methyldiethoxysilane, (3-acryloxypropyl)methyldimethoxysilane, (3-acryloxypropyl)trimethoxysilane, (3-methacrylamidopropyl)trimethoxysilane, (methacryloxymethyl)dimethylethoxysilane, (methacryloxymethyl)methyldimethoxysilane, (methacryloxymethyl) methyldiethoxysilane, 3-acrylamidopropyltrimethoxysilane, acryloxymethyltrimethoxysilane, methacryloxymethyltriethoxysilane, methacryloxymethyltrimethoxysilane, methacryloxypropyldimethylethoxysilane, methacryloxypropyldimethylmethoxysilane, methacryloxypropylmethyldiethoxysilane, methacryloxypropylmethyldimethoxysilane, methacryloxypropyltriethoxysilane, methacryloxypropyltrimethoxysilane, or a combination thereof.

* * * * *